United States Patent [19]

Locht et al.

[11] Patent Number: 5,786,189

[45] Date of Patent: Jul. 28, 1998

[54] VACCINE

[75] Inventors: Camille Locht, Wannehain, France; Yves Lobet, Rixensart, Belgium

[73] Assignee: SmithKline Beecham Biologicals (S.A.), Rixensart, Belgium

[21] Appl. No.: 763,460

[22] Filed: Dec. 11, 1996

Related U.S. Application Data

[63] Continuation of Ser. No. 245,848, May 19, 1994, abandoned, which is a continuation of Ser. No. 852,212, filed as PCT/EP90/02034, Nov. 26, 1990, 1992, abandoned, which is a continuation-in-part of Ser. No. 455,648, Dec. 22, 1989, abandoned, which is a continuation-in-part of Ser. No. 442,808, Nov. 29, 1989, abandoned.

[51] Int. Cl.$^6$ ............... C12N 15/11; C12N 15/31; C12N 15/70; A61K 39/10

[52] U.S. Cl. ............. 435/172.3; 435/69.1; 435/193; 435/252.3; 435/252.31; 435/252.33; 435/252.35; 435/254.2; 435/320.1; 424/200.1; 424/254.1; 530/403; 536/23.7

[58] Field of Search ............... 424/200.1, 254.1; 435/172.3, 193, 69.1, 252.3, 252.31, 252.33, 252.35, 254.2, 320.1; 530/403; 536/23.7

[56] References Cited

U.S. PATENT DOCUMENTS

| | | | |
|---|---|---|---|
| 4,883,761 | 11/1989 | Keith et al. | 435/252.33 |
| 5,000,952 | 3/1991 | Steinman et al. | 424/190.1 |
| 5,085,862 | 2/1992 | Klein et al. | 424/197.11 |
| 5,221,618 | 6/1993 | Klein et al. | 435/69.1 |
| 5,244,657 | 9/1993 | Klein et al. | 435/193 |
| 5,332,583 | 7/1994 | Klein et al. | 424/190.1 |
| 5,358,868 | 10/1994 | Klein et al. | 435/243 |
| 5,427,788 | 6/1995 | Rappuoli et al. | 424/190.1 |
| 5,433,945 | 7/1995 | Klein et al. | 424/185.1 |
| 5,439,810 | 8/1995 | Loosmore et al. | 435/69.3 |

FOREIGN PATENT DOCUMENTS

| | | |
|---|---|---|
| 0 275 689 | 7/1988 | European Pat. Off. . |
| 281530 | 9/1988 | European Pat. Off. . |
| 296765 | 12/1988 | European Pat. Off. . |
| 0 306 318 | 3/1989 | European Pat. Off. . |
| 322115 | 6/1989 | European Pat. Off. . |
| 0 322 533 | 7/1989 | European Pat. Off. . |
| 0352250 | 1/1990 | European Pat. Off. . |
| 0 396 964 | 11/1990 | European Pat. Off. . |
| WO 91/08294 | 6/1991 | WIPO . |

OTHER PUBLICATIONS

Bowie, et al., "Deciphering the Message in Protein Sequences: Tolerance to Amino Acid Substitutions", (1990), Science, 247, pp. 1306–1310.

Pizza et al., "Bacterial Toxins Protein", (1990), Rappuoli et al. (Eds.), pp. 507–518, Gustav Fischer, Stuttgart, NY.

Schmidt et al. (1989) Infect Immun., 57:438–445.

Burnette et al. (1988), Biotechnology, 6:699–706.

Ui, M., "The Multiple Biological Activated Pertussis Toxin, in Patho Genesis and Immunity in Pertussis", (1988), Wardlaw et al. (Eds.), pp. 121–144, John Wiley and Sons.

Black et al., (1987), Infection and Immunity, vol. 55, pp. 2465–2470.

Kunkel et al., (1987), Methods in Enzymology, vol. 154, pp. 367–382.

Armstrong et al. (1987), Infection and Immunity, vol. 55, pp. 1294–1299.

Locht et al. (1986), Science, vol. 232, pp. 1258–1264.

Locht et al. (1987), Infection and Immunity, vol. 55, pp. 2546–2553.

Capiau et al. (1986), Febs Letter, vol. 204, pp. 336–340.

Stibitz et al., (1986), Gene, 50: 133–140.

*Primary Examiner*—Robert A. Wax
*Assistant Examiner*—William W. Moore
*Attorney, Agent, or Firm*—Alissa M. Eagle; William T. King; Edward T. Lentz

[57] ABSTRACT

The *Bordetella pertussis* toxin is genetically modified to express a toxin protein which is deficient in target-cell receptor binding and is used in a vaccine for protection against whooping cough.

31 Claims, No Drawings

VACCINE

This is a continuation of application Ser. No. 08/245,848, filed May 19, 1994, now abandoned, which is a continuation of U.S. Ser. No. 07/852,212, filed May 29, 1992, now abandoned, which is a continuation of application Ser. No. PCT/EP90/02034, filed Nov. 26, 1990, which is a continuation in part of U.S. Ser. No. 07/455,648, filed Dec. 22, 1989, now abandoned, which is a continuation in part of U.S. Ser. No. 07/442,808, filed Nov. 29, 1989, and now abandoned.

FIELD OF THE INVENTION

This invention relates to genetic modifications of the Bordetella pertussis toxin and to a vaccine comprising an immunoprotective amount of such protein.

BACKGROUND OF THE INVENTION

The members of the genus Bordetella are pathogenic microorganisms involved in the infection of the respiratory tract. The genus is comprised of four species; B. pertussis, B. parapertussis, B. bronchiseptica, and B. avium. The most virulent species to man is B. pertussis, which is the etiologic agent of whooping cough.

Current conventional pertussis vaccines contain whole but inactivated B. pertussis cells. Such cells are inactivated by treatment at 56° C. for 30 minutes and/or treatment with formaldehyde. In spite of inactivation, such whole cell vaccines retain a substantial amount of toxicity.

As a result, alternate pertussis vaccines are available which are prepared from avirulent or toxin-deficient strains of B. pertussis. However, these vaccines have proven to be much less protective than those prepared from virulent strains. See, for example, Wardlaw et al., J Med Microbiol 9: 89–100 (1976).

B. pertussis produces a number of toxins (pertussis toxin, adenylate cyclase, dermonecrotic toxin, and tracheal cytotoxin) which destroy the clearance mechanisms of the respiratory tract, or interfere with the immune response (F. Mooi, Antonie van Leeuwenhoek, 54: 465–474 (1988)). A wide variety of biological activities, such as histamine sensitization, insulin secretion, lymphocytosis promotion and immunopotentiating effects can be attributed to the pertussis toxin (J. Munoz, in Pertussis Toxin, p 1–18, Sekura et al., Eds., Academic Press, New York, 1985). In addition, it has been shown that the administration of the B. pertussis toxin in mice protected them against subsequent challenge (Munoz et al., Infect Immun 32: 243–250 (1981)). Pertussis toxin is therefore an important constituent in a vaccine against whooping cough and is included in the acellular component vaccines being tested and used in several countries (Sato et al., Lancet, 1984-I: 122 (1984)). Paradoxically, the pertussis toxin, which is capable of eliciting an immune response, may itself be responsible for the harmful side effects associated with current vaccines (Steinman et al., Proc. Natl Acad Sci USA, 82: 8733 (1985)). These harmful effects can range from simple flushing to permanent neurological damage and in some instances, death.

The pertussis toxin is composed of five different subunits, designated S1 to S5 based on their electrophoretic migration in SDS-polyacrylamide gels. The subunits associate in the molar ratio of 1:1:1:2:1, respectively, to form the holotoxin. Functionally, the pertussis toxin can be divided into the A protomer, or S1 subunit, which contains adenosine diphosphate (ADP)-ribosylation activity, and the B-oligomer, comprised of subunits S2 through S5, which contains target cell receptor binding activities. Thus the B-oligomer is essential in bringing the A protomer into contact with the target-cell's membrane.

Locht et al., Science 232: 1258–64 (1986), disclose that the subunits of the pertussis toxin are encoded by closely linked cistrons. Locht et al. further disclose the nucleotide sequence of the B. pertussis toxin gene and the amino acid sequences for the individual subunits.

Locht et al., NAR 14: 3251–61 (1986), reveal the cloning of a 4.5 kb DNA fragment from the B. pertussis toxin gene containing at least the S4 subunit and a portion of another subunit gene. Sequence analysis revealed that the mature S4 subunit is derived by proteolytic cleavage of a precursor molecule.

Nicosia et al., Infect Immun 55: 963–7 (1987), disclose expression of each of the five B. pertussis toxin subunits as fusions to DNA polymerase MS2. Antisera raised to these proteins were found not to be immunoprotective in vivo or in vitro.

Locht et al., Infect Immun 55: 2546–2553 (1987), disclose the expression of the S1 and S2 subunits of pertussis toxin in E. coli as fusions to 6 amino acid residues of beta-gacactosidase followed by 5 amino acids encoded by a polylinker. It was disclosed that the recombinant S1 subunit displayed enzymatic activities. A truncated version of the S1 subunit was disclosed in which the last 48 amino acid residues, i.e., the carboxy terminus, was deleted.

Sclavo SpA, EP-A-232,229, published Aug. 12, 1987, disclose the cloning and expression of a B. Pertussis toxin gene, which contains subunits S1 through S5 in E. coli.

Bellini et al., EP-A-281,530, published Sep. 7, 1988, disclose expression of mature B. pertussis subunits in B. subtilis.

Burnette et al., EP-A-306,318, published Mar. 8, 1989, report the subcloning and expression of individual B. pertussis toxin subunits in E. coli. Burnette et al. disclose that the S4 subunit could only be expressed upon removal of the signal peptide coding sequence. Burnette et al. also disclose S1 subunit analogs expressed in E. coli with modifications between amino acids $Val^7$ to $Pro^{14}$.

Burns et al., U.S. Pat. No. 4,845,036, disclose a method for isolating the wild-type B. pertussis B-oligomer (i.e., subunits S2–S5) by dissociation of the holotoxin (i.e., subunits S1–S5).

Sato et al., EP-A-296,765, published Dec. 28, 1988, disclose B. pertussis variants which produce mutant pertussis toxin proteins. The variants arose from exposure of virulent B. pertussis with nitrosoguanidine, a known mutagen.

M. Ui, (in Pathogenesis and Immunity in Pertussis, Wardlaw et al., eds., p. 121–145, Wiley & Sons, Chichester, 1988) discloses that certain chemical modifications, e.g., acylation, of the pertussis toxin lysine residues eliminate all biological activity. Methylation of the pertussis toxin, which also modifies lysine residues, does not affect the ADP-ribosylation activity but does reduce or abolish certain biological activities associated with the B-oligomer, for example, mitogenic activity, stimulation of glucose oxidation, promotion of lymphocytosis and histamine-sensitizing activity. Ui further discloses that methylation of dimer D2(i.e., pertussis toxin subunits S3–S4), but not dimer D1 (i.e., pertussis toxin subunits S2–S4) or subunit S5, eliminates the mitogenic activity associated with the B-oligomer. There is no disclosure or suggestion, however, as to which specific regions or specific lysine residues of the B-oligomer are involved in the methylation or acylation.

Hausman et al., Infect Immun 57: 1760–64 (1989), disclose immunization of mice with the pertussis toxin dimeric subunits, D1 (i.e., S2–S4) and D2 (i.e., S3–S4). The antisera raised to these dimers were able to recognize B. pertussis toxin and neutralize its toxic effects in vitro.

Capiau et al., U.S. patent application Ser. No. 07/222,991, *filed Jul. 22, 1988 disclose modification of the B. pertussis toxin S1 subunit at amino acid position 26 (i.e., tryptophan). This residue can be modified either chemically or by site-directed mutagenesis to substantially inactivate the enzymatic activity of the S1 subunit.

Bellini et al., Gene, 69: 325–330 (1988), recite a general method for site-directed mutagenesis for double-stranded plasmid DNA. Bellini et al. disclose that their method is particularly valuable where long deletions are needed. Exemplified is the deletion of the B. pertussis S2 subunit signal sequence coding region located on an E. coli—B. subtilis shuttle vector.

Black et al., EP-A-275, 689, published Jul. 27, 1988 and Infect Immun 55: 2465–70 (1987), disclose expression of the S4 subunit in E. coli. In addition, Black et al. disclose mutations in the B. pertussis toxin gene that were either deletions generated by Bal31 exonuclease or insertions with the kanamycin resistance gene. These mutations were then introduced by allelic exchange into the B. pertussis chromosome.

Klein et al., EP-A-322,115, published Jun. 28, 1989, disclose substitution mutations of the B. pertussis toxin. Klein et al. also disclose deletion mutations of the S1 subunit. However, of the deletion mutations disclosed, only one mutation, Glu$^{129}$, was weakly reactive against antibodies to the S1 subunit.

It is an object of this invention to provide an improved B. pertussis vaccine comprising a modified B. pertussis toxin or subunits thereof which are immunogenic, yet non-toxic.

SUMMARY OF INVENTION

The present invention relates to a recombinant DNA molecule which encodes a protein specifically reactive with antibodies against the wild-type pertussis toxin but which is defective in pertussis toxin target cell receptor binding.

In related aspects, this invention is a recombinant plasmid which comprises the recombinant DNA molecule of this invention operatively linked to a regulatory region. Said regulatory region contains regulatory sequences necessary for transcription of the protein coding sequence and subsequent translation in a host cell transformed with the recombinant plasmid of the invention.

This invention also relates to a pertussis toxin protein encoded by the recombinant DNA molecule of the invention, which is specifically reactive with antibodies against the wild-type pertussis toxin but which is also defective in pertussis toxin target cell receptor binding.

In another aspect, this invention is a vaccine for stimulating protection against whooping cough wherein such vaccine comprises an immunoprotective and non-toxic quantity of the protein encoded by the recombinant DNA molecule of the invention For vaccinal purposes, the protein of the invention may be purified away from the host cell or cell culture medium, or alternatively, it may be associated with the outer surface membrane of the host cell.

This invention further relates to a process for preparing the protein of the invention. This process comprises growing a host cell transformed with the recombinant DNA molecule of this invention in a suitable culture medium.

DETAILED DESCRIPTION OF THE INVENTION

The present invention is based on the discovery that modification of one or more of the naturally occurring amino acid residues of the Bordetella pertussis toxin B-oligomer DNA coding sequence greatly reduces the binding of pertussis toxin to target cell receptors thereby greatly reducing the toxicity of the pertussis toxin while retaining its ability to elicit a protective immunogenic response.

Many, but not all of the biological activities of the pertussis toxin (PT) are the result of three essential molecular steps. The first step involves the binding of PT to the receptors on the target cell membranes via the B-oligomer (subunits S2 through S5). Next, the S1 subunit must translocate into the cytoplasm of the target cell. Finally, the internalized S1 subunit has to express its enzymatic activity which includes NAD-glycohydrolysis and ADP-ribosylation. (For a review, see Ui, M., in Pathogenesis and Immunity in Pertussis, p. 121–145, Wardlaw and Parton, eds., Wiley and Sons, Chichester, 1988). Elimination of any of these three steps drastically diminishes the biological activities of said toxin. Therefore, a modified pertussis toxin which is incapable of binding to target cell receptors, drastically reduces or eliminates the toxic activities associated with the pertussis toxin.

The B-oligomer, which is associated with adherence or binding of PT to host cells, is composed of subunits S2–S5. The B-oligomer can be further divided into two dimers, D1 and D2, which are connected by subunit S5. Dimer D1 comprises subunits S2 and S4, whereas dimer D2 comprises subunits S3 and S4 (see, Tamura et al., Biochemistry, 21: 5516–22 (1982)). Each dimer specifically interacts with different target cell receptor molecules. For example, D1 appears to be responsible for the binding of PT to such glycoproteins as haptoglobin or fetuin (see, Francotte et al., in Vaccine 89, p. 243–247, Lerner et al., eds., Cold Spring Harbor Laboratory, Cold Spring Harbor, N.Y., 1989), :whereas D2 can specifically bind to Chinese Hamster Ovary (CHO) cell membranes (see, Brennan et al., J Biol Chem, 263: 4895–99 (1988)). It is presumed that this binding specificity is attributed to the structural differences between S2 and S3.

The nucleotide sequence for the Bordetella pertussis toxin gene is disclosed by Locht et al. (Science, 232: 1258–64 (1986)):

```
  1 GAATTCGTCG CCTCGCCCTG GTTCGCCGTC ATG-
    GCCCCCA AGGGAACCGA
 51 CCCCAAGATA ATCGTCCTGC TCAACCGCCA CAT-
    CAACGAG GCGCTGCAGT
101 CCAAGGCGGT CGTCGAGGCC TTTGCCGCCC
    AAGGCGCCAC GCCGGTCATC
151 GCCACGCCGG ATCAGACCCG CGGCTTCATC
    GCAGACGAGA TCCAGCGCTG
201 GGCCGGCGTC GTGCGCGAAA CCGGCGCCAA
    GCTGAAGTAG CAGCGCAGCC
251 CTCCAACGCG CCATCCCCGT CCGGCCGGCA
    CCATCCCGCA TACGTGTTGG
301 CAACCGCCAA CGCGCATGCG TGCAGATTCG
    TCGTACAAAA CCCTCGATTC
351 TTCCGTACAT CCCGCTACTG CAATCCAACA
    CGGCATGAAC GCTCCTTCGG
401 CGCAAAGTCG CGCGATGGTA CCGGTCACCG
    TCCGGACCGT GCTGACCCCC
451 CTGCCATGGT GTGATCCGTA AAATAGGCAC
    CATCAAAACG CAGAGGGGAA
501 GACGGGATGC GTTGCACTCG GGCAATTCGC
    CAAACCGCAA GAACAGGCTG
```

```
 551 GCTGACGTGG CTGGCGATTC TTGCCGTCAC
     GGCGCCCGTG ACTTCGCCGG
 601 CATGGGCCGA CGATCCTCCC GCCACCGTAT
     ACCGCTATGA CTCCCGCCCG
 651 CCGGAGGAGG TTTTCCAGAA CGGATTCACG
     GCGTGGGGAA ACAACGACAA
 701 TGTGCTCGAC CATCTGACCG GACGTTCCTG
     CCAGGTCGGC AGCAGCAACA
 751 GCGCTTTCGT CTCCACCAGC AGCAGCCGGC
     GCTATACCGA GGTCTATCTC
 801 GAACATCGCA TGCAGGAAGC GGTCGAGGCC
     GAACGCGCCG GCAGGGGCAC
 851 CGGCCACTTC ATCGGCTACA TCTACGAAGT
     CCGCGCCGAC AACAATTTCT
 901 ACGGCGCCGC CAGCTCGTAC TTCGAATACG
     TCGACACTTA TGGCGACAAT
 951 GCCGGCCGTA TCCTCGCCGG CGCGCTGGCC
     ACCTACCAGA GCGAATATCT
1001 GGCACACCGG CGCATTCCGC CCGAAAACAT
     CCGCAGGGTA ACGCGGGTCT
1051 ATCACAACGG CATCACCGGC GAGACCACGA
     CCACGGAGTA TTCCAACGCT
1101 CGCTACGTCA GCCAGCAGAC TCGCGCCAAT
     CCCAACCCCT ACACATCGCG
1151 AAGGTCCGTA GCGTCGATCG TCGGCACATT
     GGTGCATGGC GCCGGTGATA
1201 GCGCTTGCAT GGCGCGGCAG GCCGAAAGCT
     CCGAGGCCAT GGCAGCCTGG
1251 TCCGAACGCG CCGGCGAGGC GATGGTTCTC
     GTGTACTACG AAAGCATCGC
1301 GTATTCGTTC TAGACCTGGC CCAGCCCCGC
     CCAACTCCGG TAATTGAACA
1351 GCATGCCGAT CGACCGCAAG ACGCTCTGCC
     ATCTCCTGTC CGTTCTGCCG
1401 TTGGCCCTCC TCGGATCTCA CGTGGCGCGG
     GCCTCCACGC CAGGCATCGT
1451 CATTCCGCCG CAGGAACAGA TTACCCAGCA
     TGGCAGCCCC TATGGACGCT
1501 GCGCGAACAA GACCCGTGCC CTGACCGTGG
     CGGAATTGCG CGGCAGCGGC
1551 GATCTGCAGG AGTACCTGCG TCATGTGACG
     CGCGGCTGGT CAATATTTGC
1601 GCTCTACGAT GGCACCTATC TCGGCGGCGA
     ATATGGCGGC GTGATCAAGG
1651 ACGGAACACC CGGCGGCGCA TTCGACCTGA
     AAACGACGTT CTGCATCATG
1701 ACCACGCGCA ATACGGGTCA ACCCGCAACG
     GATCACTACT ACAGCAACGT
1751 CACCGCCACT CGCCTGCTCT CCAGCACCAA
     CAGCAGGCTA TGCGCGGTCT
1801 TCGTCAGAAG CGGGCAACCG GTCATTGGCG
     CCTGCACCAG CCCGTATGAC
1851 GGCAAGTACT GGAGCATGTA CAGCCGGCTG
     CGGAAAATGC TTTACCTGAT
1901 CTACGTGGCC GGCATCTCCG TACGCGTCCA
     TGTCAGCAAG GAAGAACAGT
1951 ATTACGACTA TGAGGACGCA ACGTTCGAGA
     CTTACGCCCT TACCGGCATC
2001 TCCATCTGCA ATCCTGGATC ATCCTTATGC
     TGAGACGCTT CCCCACTCGA
2051 ACCACCGCCC CGGGACAGGG CGGCGCCCGG
     CGGTCGCGCG TGCGCGCCCT
2101 GGCGTGGTTG CTGGCATCCG GCGCGATGAC
     GCATCTTTCC CCGCCCTGG
2151 CCGACGTTCC TTATGTGCTG GTGAAGACCA
     ATATGGTGGT CACCAGCGTA
2201 GCCATGAAGC CGTATGAAGT CACCCCGACG
     CGCATGCTGG TCTGCGGCAT
2251 CUCCGUCAAA CTGGGCGCCG CGGCCAGCAG
     CCCGGACGCG CACGTGCCGT
2301 TCTGCTTCGG CAAGGATCTC AAGCGTCCCG
     GCAGCAGTCC CATGGAAGTC
2351 ATGTTGCGCG CCGTCTTCAT GCAACAACGG
     CCGCTGCCGCA TGTTTCTGGG
2401 TCCCAAGCAA CTCACTTTCG AAGGCAAGCC
     CGCGCTCGAA CTGATCCGGA
2451 TGGTCGAATG CAGCGGCAAG CAGGATTGCC
     CCTGAAGGCG AACCCCATGC
2501 ATACCATCGC ATCCATCCTG TTGTCCGTGC
     TCGGCATATA CAGCCCGGCT
2551 GACGTCGCCG GCTTGCCGAC CCATCTGTAC
     AAGAACTTCA CTGTCCAGGA
2601 GCTGGCCTTG AAACTGAAGG GCAAGAATCA
     GGAGTTCTGC CTGACCGCCT
2651 TCATGTCGGG CAGAAGCCTG GTCCGGGCGT
     GCCTGTCCGA CGCGGGACAC
2701 GAGCACGACA CGTGGTTCGA CACCATGCTT
     GGCTTTGCCA TATCCGCGTA
2751 TGCGCTCAAG AGCCGGATCG CGCTGACGGT
     GGAAGACTCG CCGTATCCGG
2801 GCACTCCGG CGATCTGCTC GAACTGCAGA
     TCTGCCCGCT CAACGGATAT
2851 TGCGAATGAA CCCTTCCGGA GGTTTCGACG
     TTTCCGCGCA ATCCGCTTGA
2901 GACGATCTTC CGCCCTGGTT CCATTCCGGG
     AACACCGCAA CATGCTGATC
2951 AACAACAAGA AGCTGCTTCA TCACATTCTG
     CCCATCCTGG TGCTCGCCCT
3001 GCTGGGCATG CGCACGGCCC AGGCCGTTGC
     GCCAGGCATC GTCATCCCGC
3051 CGAAGGCACT GTTCACCCAA CAGGGCGGCG
     CCTATGGACG CTGCCCGAAC
3101 GGAACCCGCG CCTTGACCGT GGCCGAACTG
     CGCGGCAACG CCGAATTGCA
3151 GACGTATTTG CGCCAGATAA CGCCCGGCTG
     GTCCATATAC GGTCTCTATG
3201 ACGGTACGTA CCTGGGCCAG GCGTACGGCG
     GCATCATCAA GGACGCGCCG
3251 CCAGGCGCGG GGTTCATTTA TCGCGAAACT
     TTCTGCATCA CGACCATATA
3301 CAAGACCGGG CAACCGGCTG CGGATCACTA
     CTACAGCAAG GTCACGGCCA
3351 CGCGCCTGCT CGCCAGCACC AACAGCAGGC
     TGTGCGCGGT ATTCGTCAGG
3401 GACGGGCAAT CGGTCATCGG AGCCTGCGCC
     AGCCCGTATG AAGGCAGGTA
3451 CAGAGACATG TACCACGCGC TGCGGCGCCT
     GCTGTACATG ATCTATATGT
3501 CCGGCCTTGC CGTACGCGTC CACGTCAGCA
     AGGAAGAGCA GTATTACGAC
3551 TACGAGGACG CCACATTCCA GACCTATGCC
     CTCACCGGCA TTTCCCTCTG
3601 CAACCCGGCA GCGTCGATAT GCTGAGCCGC
     CGGCTCGGAT CTGTTCGCCT
3651 GTCCATGTTT TTCCTTGACG GATACCGCGA
     ATGAATCCCT TGAAAGACTT
3701 GAGAGCATCG CTACCGCGCC TGGCCTTCAT
     GGCAGCCTGC ACCCTGTTGT
3751 CCGCCACGCT GCCCGACCTC GCCCAGGCCG
     GCGGCGGGCT GCAGCGCTGT
3801 CAACCACTTC ATGGCGAGCA TCGTGGTCGT
     ACTGCCGCGG CGGTCAGTGG
3851 CCACGGTGAC CATCGCCATA ATCTGGGCGG
     GCTACAAGCT GCTGTTCCCG
3901 CACGCCGATG TGCTGGACGT GGTGCGTGTG
     GTGCTGGCGG GAGCTGCTGA
```

```
3951 TCGGCGCATC GGCCGAAATC GCTCGTTATC
     TGCTGACCTG AATCCTGGAC
4001 GTATCGAACA TGCGTGATCC GCTTTTCAAG
     GGCTGCACCC GGCGCCGCGA
4051 TGCTGATGGC GTACCCGCCA CGGCAGGCCG
     TGTGCAGCCG GCACCATTCC
4101 CTGCTGGGCC ATCTCGGTTC AGCATCCGCT
     TTCTGGCCTT GTTTCCCGTG
4151 GCATTGCTGG CGATGCGGAT CATGATCCGG
     CGCGATGACC AGCAGTTCCG
4201 CCTGATC
```

Wherein: the S1 subunit is encoded by nucleotides 507 to 1310; the mature S1 subunit is encoded by nucleotides 609 to 1310. The S2 subunit is encoded by nucleotides 1353 to 2030; the mature S2 subunit is encoded by nucleotides 1434 to 2030. The S4 subunit is encoded by nucleotides 2090 to 2482; the mature S4 subunit is encoded by nucleotides 2153 to 2482. The S5 subunit is encoded by nucleotides 2497 to 2856; the mature S5 subunit is encoded by nucleotides 2557 to 2856. The S3 subunit is encoded by nucleotides 2942 to 3622; the mature S3 subunit is encoded by nucleotides 3026 to 3622.

S2 and S3 are 70% homologous in their amino acid sequences and 75% homologous in their nucleotide sequences (see, Locht et al., *Science*, 232: 1258–64 (1986)). Despite their homology, S2 and S3 cannot substitute for each other in the functionally active pertussis toxin (see, Tamura et al., supra). In addition, each of the S2 and S3 subunits bind to one S4 subunit. Hence the two dimers, D1 and D2, must be closely related to each other though their roles in B-oligomer function are quite distinct.

Chemical modification of the pertussis toxin can affect its biological activities. Acylation, for example, eliminates all biological activity-associated with the pertussis toxin due to disruption of the quaternary structure (see, Nogimori et al., *Biochim Biophys Acta*, 801: 220–231 (1984)). Methylation of the pertussis toxin, which modifies lysine residues, does not affect the ADP-ribosylation activity but does reduce or abolish activity associated with the B-oligomer (see Ui, M., in *Pathogenesis and Immunity in Pertussis*, p. 121–145, Wardlaw and Parton, eds., Wiley and Sons, Chichester, 1988). Furthermore, Ui discloses that methylation of dimer D2, but not dimer D1 or subunit S5, eliminates the mitogenic activity associated with the B-oligomer. Therefore, Ui concludes that the lysine residues play a role in the attachment of D2 to the host cell's surface, but not the attachment of D1.

It has also been shown that iodination of pertussis toxin severely reduces some biological activities, such as hemagglutination and CHO cell clustering. See, Armstrong et al., *Infect Immun*, 55: 1294–99 (1987). Armstrong et al. also disclose a method to radioiodinate the wild-type pertussis toxin in the presence of fetuin-agarose and still retain biological activity. It was reported that by using such method, all of the PT subunits were iodinated. However, Armstrong et al. report that the mechanism for the observed reduction in biological activity is not known.

The present invention thus describes a *B. pertussis* toxin DNA sequence which encodes a protein which is defective in target cell receptor binding activity and preferably lacks S1 subunit enzymatic activity as well, yet retains the capability to be recognized by anti-Pertussis Toxin antibodies.

Target cell receptor binding activity can be assayed by haptoglobin-binding as described by Francotte et al. (in *Vaccine* 89, p.243–247, Lerner et al., eds., Cold Spring Harbor Laboratory, Cold Spring Harbor, N.Y., 1989) or by CHO cell binding/cytotoxicity assays as described by Brennan et al. (*J Biol Chem*, 263: 4895–99 (1988)) or Burns et al. (*Infect Immun*, 55: 24 (1987)). S1 subunit enzymatic activity can be measured by the ADP-ribosylation assay as described by Burnette et al. (*Science*, 242: 72 (1988)).

DNA molecules comprising the recombinant DNA molecule of this invention can be derived from any *B. pertussis* strain using known techniques, e.g., isolating the gene from a gene bank, making complementary or cDNAs from a mRNA template or via the polymerase chain reaction (see, U.S. Pat. No. 4,800,159) or from isolates of clinical specimens. Alternatively, such recombinant DNA molecule may be synthesized by standard DNA synthesis techniques. Furthermore, various *B. pertussis* strains are publicly available from commercial depositories, e.g., from the American Type Culture Collection (ATCC), Rockville, Md., U.S.A.

As used herein, the term "DNA sequence which encodes a protein specifically reactive with antibodies against wild-type pertussis toxin but which is defective in pertussis toxin target cell receptor binding" means a DNA coding sequence which encodes a protein with decreased target cell binding activity relative to the wild-type pertussis toxin but still retains the ability to be recognized by anti-pertussis toxin antibodies, such as a coding sequence which encodes a protein comprising all the subunits (S1, S2, S3, S4 and S5) substantially as described by Locht et al. (*Science* 232: 1258–64 (1986)) and all mutations or mutants thereof. The terms "mutations" or "mutants" as applied to the B oligomer or S2 or S3 subunits encompass any derivative of the recombinant DNA molecule of this invention which encodes a protein which is defective in target cell receptor binding and still retains the ability to be recognized by anti-Pertussis Toxin antibodies. Such mutations can be prepared by the deletion, addition, substitution, or rearrangement of amino acids and their nucleic acid coding sequences, or alternatively, by chemical modifications thereof.

Preferred embodiments of the recombinant DNA molecule of this invention include, but are not limited to, a recombinant DNA molecule containing amino acid deletions in $Asn^{105}$, or $Tyr^{102}$, or $Tyr^{102-103}$ of subunit S2, and/or $Lys^{10}$, or $Tyr^{92}$, or $Lys^{93}$, or $Lys_{105}$, or $Tyr^{102}$, or $Tyr^{102-103}$ of subunit S3, or single amino acid substitutions, e.g., $Asn^{105}$ to Asp of subunit S2.

The most preferred embodiments include, but are not limited to deletions of $Asn^{105}$, or $Tyr^{102}$, or $Tyr^{102-103}$ in subunit S2 and/or $Lys^{105}$, or $Tyr^{102}$, or $Tyr^{102-103}$ in subunit S3.

Mutations in S1 (e.g., deletions of $Trp^{26}$, or $His^{35}$, or $Ser^{40}$, or $Glu^{129}$) are disclosed in U.S. application Ser. No. 07/381,888,* filed Jul. 18, 1989, the entire disclosure of which is hereby incorporated by reference herein. Mutations of other S1 subunit amino acid residues (i.e., substitutions of $Arg^9$, $Arg^{13}$, $Glu^{129}$) are disclosed by Pizza et al., *Science*, 246: 497–500 (1989) and EP-A-O 396 964, and also in EP-A-0306318. These references are incorporated by reference herein.

*EP-A-0 352 250

Preferably the DNA coding sequence of this invention will encode a protein that resembles the natural or wild-type protein as much as possible in tertiary structure, i.e., a protein which is able to be recognized by anti-pertussis toxin antibodies, yet is deficient in target cell receptor binding activity.

Other embodiments of the recombinant DNA molecule of this invention include a pertussis toxin coding sequence which encodes some, but not all of the subunits. Exemplary embodiments include, but are not limited to, D1 (S2 and S4), D2 (S3 and S4), S1-S2-S4, S1-S3-S4 and the B-oligomer (S2, S3, S4 and S5).

In another embodiment; the recombinant DNA molecule of the invention can be in the form of a hybrid, that is, a coding sequence which encodes a fusion polypeptide containing additional sequences which can carry one or more epitopes from other PT subunits, for example, [S2 epitope]-[S3 subunit], etc., other *B. pertussis* antigens, or other non-*B. pertussis* antigens. Alternatively, the recombinant DNA molecule of the invention can be fused to the DNA coding sequence of a carrier polypeptide which has immunostimulating properties, as in the case of an adjuvant, or which otherwise enhances the immune response to the *B. pertussis* toxin subunit(s), or which is useful in expressing, purifying or formulating the *B. pertussis* toxin subunit(s).

The recombinant DNA molecule of this invention may comprise additional DNA sequences, including e.g., a regulatory element, one or more selectable markers, and sequences that code for replication and maintenance functions. The regulatory region typically contains a promoter found upstream from the coding sequence of this invention, which functions in the binding of RNA polymerase and in the initiation of RNA transcription. In other words, the regulatory element or region is operatively linked to the coding sequence of this invention. It will be appreciated by one of skill in the art that the selection of regulatory regions will depend upon the host cell employed.

This invention also relates to a recombinant DNA plasmid comprising the recombinant DNA molecule of this invention.

Another aspect of this invention is a host cell transformed with the recombinant DNA molecule of this invention. Such host cell is capable of growth in a suitable culture medium and expressing the coding sequence of the invention. Such host cell is prepared by the method of this invention, i.e., by transforming a desired host cell with the plasmid of this invention. Such transformation is accomplished by utilization of conventional transformation techniques. Moreover, the recombinant DNA molecule of this invention can be integrated into the host cell's genome by conventional techniques, e.g., homologous recombination. The most preferred host cells of this invention include those belonging to the species *E. coli* and the genus Bordetella. Other host cells which may be suitable include, but are not limited to, mammalian cells, insect cells, yeast and other bacterial cells, e.g., Streptomyces, Bacillus and Salmomella. Thus, this invention and the product thereof is not limited to any specific host cell.

The present invention also relates to a protein encoded by the recombinant DNA molecule of this invention. Preferably such protein is produced by the transformed host cell of this invention, but such protein may be prepared by conventional peptide synthesis techniques.

The protein of this invention preferably has no more than about 50% of the haptoglobin binding or CHO cytotoxicity as compared to wild-type pertussis toxin. Most preferably, the protein of this invention has less than 10% and more preferably less than 5% of either of the assayed activities as compared to wild-type pertussis toxin.

The present invention also relates to a method of producing the protein encoded by the recombinant DNA molecule of this invention which comprises culturing the transformed host of the invention in an appropriate culture media and the isolation of such protein. By "appropriate culture media" is meant that media which will enable such host to express the coding sequence of the invention in recoverable quantity. It will be appreciated by one of skill in the art that the appropriate culture media to use will depend upon the host cell employed. The isolation of the protein so produced is accomplished from a culture lysate of the host, or if appropriate, directly from the host's culture medium, and such isolation is carried out by conventional protein isolation techniques. See, for example, Burns et al., U.S. Pat. No. 4,845,036.

In a preferred embodiment of this invention, the coding sequence of the protein of the invention is expressed in a transformed *B. pertussis* host cell to produce an immunogenic yet substantially inactivated protein, i.e., a protein that is deficient in target-cell receptor binding, and in addition, may optionally be deficient in ADP-ribosyltransferase activity, but which is still specifically recognized by anti-Pertussis Toxin antibodies. In such a system, sequences that encode *B. pertussis* toxins are typically located on a suicide vector. Such suicide vector contains a sufficient amount of bacterial DNA to propagate the suicide vector in *E. coli* or some other suitable host. Such suicide vector also contains a sufficient amount of *B. pertussis* DNA flanking the toxin subunit coding sequence so as to permit recombination between a *B. pertussis* host deficient in the toxin gene and the heterologous toxin gene. It is understood to one skilled in the art that it is not essential to use a *B. pertussis* host deficient in the toxin gene, but that the absence of the toxin gene in the host prior to recombination will facilitate the screening and isolation of recombinant hosts which have incorporated the gene of interest. The recombinant *B. pertussis* arising from such homologous recombination are then selected by standard techniques. See, e.g., Stibitz et al., *Gene* 50: 133–140 (1986).

The invention also encompasses a vaccine capable of inducing immunity against whooping cough. Such vaccine comprises an immunoprotective and non-toxic amount of the protein of the invention. Such vaccine typically contains 1–500 µg, preferably 5–25 µg of the protein of this invention, but is not limited to use of these amounts.

Further embodiments of the present invention include a whole cell vaccine for stimulating protection against whooping cough. Such vaccine comprises the protein of this invention expressed on the surface of transformed host cells of this invention. The transformed host cells are subsequently inactivated by conventional techniques to constitute an immunoprotective and non-toxic vaccine.

Other antigens which are known to be desirably administered in conjugation with pertussis toxin may also be included in the vaccine of this invention. Such additional components are known to those skilled in the art. Preferable additional components include tetanus toxoid and/or diptheria toxoid as well as filamentous hemagglutinin (FHA), agglutinogens 2 and 3, the 69 kD antigen, and/or any other protective antigen of *B. pertussis*.

The provision of such a vaccine thus allows for another aspect of the present invention, i.e., a method for immunizing a human against whooping cough which comprises administering the vaccine of the subject invention to such human.

The mode of administration of the vaccine of the invention may be any suitable route which delivers an immunoprotective amount of the protein of the subject invention to the host. However, the vaccine is preferably administered parenterally via the intramuscular or subcutaneous routes. Other modes of administration may also be employed, where desired, such as oral administration or via other parenteral routes, i.e., intradermally, intranasally or intravenously.

The vaccine of the invention may be prepared as a pharmaceutical composition containing an immunoprotective, non-toxic and sterile pharmaceutically acceptable carrier. In the vaccine of the invention, an aqueous solution of the protein of this invention can be used directly. Alternatively, the protein of this invention, with or without prior lyophilization, can be mixed together or with any of the various known adjuvants. Where the administration of the vaccine is parenteral, the protein of the invention can be optionally admixed or absorbed with any conventional adjuvant to enhance an immune response. Such adjuvants include among others, aluminum hydroxide, aluminum phosphate, muramyl dipeptide and saponins, such as Quil A. As a further exemplary alternative of the preparation of the vaccine of the invention, the protein of the invention can be encapsulated within microparticles such as liposomes. In yet another exemplary alternative of the preparation of the vaccine of the invention, the protein of the invention can be administered with an immunostimulating macromolecule, for example, tetanus toxoid. Alternatively, an aqueous suspension or solution containing the protein of the invention preferably is buffered at physiological pH. The protein of the invention may also be designed for oral digestion.

Vaccine preparation is generally described in *New Trends and Developments in Vaccines*, Voller et al. (eds.), University Park Press, Baltimore, Md., 1978. Encapsulation within liposomes is described by Fullerton, U.S. Pat. No. 4,235,877. Conjugation of proteins to macromolecules is disclosed, for example, by Likhite, U.S. Pat. No. 4,372,945 and Armor et al., U.S. Pat. No. 4,474,757. Use of Quil A is disclosed by Dalsgaard et al., *Acta Vet Scand* 18: 349 (1977).

It is preferred that the vaccine of the invention, when in a pharmaceutical preparation, be present in unit dosage forms. The appropriate prophylactically effective dose can be determined readily by those of skill in the art. The effective amount of protein contained in the vaccine of this invention may be in the range of effective amounts of antigen in conventional *B. pertussis* acellular or component vaccines, i.e., 5-25 µg of protein per unit dose. This dose may optionally be delivered with various amounts of filamentous hemagglutin (FHA) (approximately 10-25 µg per dose) and/or agglutinogens or other antigens. It will be understood, however, that the specific dose level for any particular patient will depend upon a variety of factors including the age, general health, the time of administration, the route of administration, synergistic effects with any other drugs being administered, and the degree of protection being sought. The administration can be repeated at suitable intervals if necessary.

The examples which follow are illustrative but not limiting of the present invention. Restriction enzymes and other reagents were used substantially in accordance with the vendors' instructions.

EXAMPLES

Modification of pertussis toxin subunits by site-directed mutagenesis:

Example 1
Mutagenesis of S2

Plasmid pPTX42, which encodes the complete nucleotide sequence for the pertussis toxin gene (Locht et al., *Science*, 232: 1258-64 (1986)) was digested with the restriction enzymes XbaI and XmaI. A 750 base pair (bp) fragment was isolated and ligated into M13mp19 previously digested with XbaI and XmaI. The vector M13mp19, which can exist as a single-stranded or a double-stranded entity, is a standard subcloning vector suitable for site directed mutagenesis and is commonly available. See J. Messing, *Meth Enzymol*, 101: 20–78 (1983). The resultant vector, designated φRIT20200, encodes the S2 subunit of pertussis toxin, plus 5'+3' untranslated DNA. This vector was then used for subsequent mutagenesis experiments.

Site-directed mutagenesis was done according to the "Oligonucleotide-Directed in vitro Mutagenesis System" (Amersham, Arlington Heights, Ill.). A synthetic oligomer directed to the region of mutagenesis was annealed to the single stranded form of φRIT20200. This annealed oligomer was then used as a primer to replicate a vector which was the complement to φRIT20200 except for specific changes made in the synthetic oligomer region. Thus, one in the art is capable of rapidly inducing specific changes in a vector without affecting the remaining nucleic acid sequences. To delete amino acid 102 (tyrosine), i.e., Tyr$^{102}$ of subunit S2, the following synthetic oligonucleotide primer was used:
5'CGTTGCTGTAGTGATCCGTT 3'
This resulting vector, which is lacking the codon for amino acid 102 (i.e., Tyr) was designated φRIT20201. It was then used for subsequent mutagenesis experiments.

To delete tyrosine 103 (Tyr$^{103}$) from φRIT20201, the following mutagenesis primer was used:
5'TGACGTTGCTGTGATCCGTT 3'
The resultant phage, lacking the codons for Tyr$^{102}$ and Tyr$^{103}$, was designated φRIT20202. To ensure that the correct mutations had occurred and that no unwanted mutations were introduced into the S2 subunit gene, the S2 subunits of both mutant vectors were sequenced. The double stranded replicative form of phages φRIT20201 and φRIT20202 were then digested with XbaI and XmaI and the 750 bp fragments encoding the 32 mutations were inserted into the XbaI and XmaI sites of plasmid pRIT13070. Plasmid pRIT13070 (Capiau et al., U.S. patent application Ser. No. 07/222,991* filed Jul. 22, 1988) is a recombinant plasmid containing the complete pertussis toxin structural gene inserted into the EcoRI site of pUC7, which is a common cloning vector (Vieira et al., *Gene*, 19: 259–68 (1982)).

* EP 0 352 250

The recombinant plasmids, containing the S2 mutations Tyr$^{102}$ and Tyr$^{102-103}$ inserted into the complete pertussis toxin structural gene, were designated pRIT13241 and pRIT13242 respectively. These plasmids were again sequenced to verify their modified nucleotide sequence.

To delete the S2 subunit codon asparagine 105 (Asn$^{105}$), the polymerase chain reaction (PCR) was used (Saiki et al., *Science* 230: 1350–1354 (1985)); the PCR system is commercially available Perkin Elmer Cetus (Emeryville, Calif.).

The mutagenesis of Asn$^{105}$ was performed as follows:
(a) Plasmid pRIT13070 was first denatured, then two synthetic oligonucleotides complementary to one strand of the denatured plasmid were annealed. The first oligonucleotide:
(I) 5'CGTTCTAGACCTGGCCCAGCCCCG3'
encodes an XbaI restriction site 5' to the site to be mutagenized, the second oligonucleotide:
(II) 5'TGGCGGTGACGCTGTAGTAG3'
spans the site to be mutagenized. The DNA between the two annealed oligonucleotides is then amplified via PCR.
(b) In the second step, two additional oligonucleotides, complementary to the opposite DNA strand of step (a), were annealed to the denatured plasmid pRIT13070. One oligonucleotide:
(III) 5'TGTCCCGGGGCGGTGGTTCGAGTG3'
encodes an XmaI restriction site 3' to the site to be mutagenized, and .the other oligonucleotide:
(IV) 5'CAGCGTCACCGCCACTCGCCTGCTCTCCAG3'
spans the site to be mutagenized and is complementary (i.e., capable of forming base pairs) with oligonucleotide (II) for a span of 14 nucleotides. The DNA between annealed oligonucleotides (III) and (IV) was then amplified via PCR. Finally, the two amplified. DNA fragments were annealed to each other and amplification of the mutagenized DNA fragment between the XbaI and XmaI sites was carried out via PCR. This amplified DNA fragment was digested with the restriction enzymes XbaI and XmaI and then inserted into the XbaI and XmaI sites of an unmutagenized pRIT13070.

To substitute the S2 subunit codon asparagine (Asn$^{105}$) with aspartic acid (Asp), the PCR system was used. The procedure is the same as the deletion of Asn$^{105}$, disclosed above, except that different oligonucleotide sequences are used. Oligomers (II) and (IV) are replaced with oligomers (IIs) and (IVs), respectively:

(IIs) 5'TGGCGGTGACGTCGCTGTAGTAG3'

(IVs) 5'CAGCGACGTCACCGCCACTCGCCT-GCTCTCCAG3'

After transformation, the recombinant mutant plasmids were analyzed by DNA sequence analysis to verify their modified nucleotide sequences.

Example 2
Mutagenesis of S3

Digestion of pPTX42 (Locht et al., cited above) with the restriction enzyme PstI yielded, among others, a 960 bp fragment containing the coding region for the S3 subunit of the pertussis toxin. This fragment was isolated and ligated into the PstI site of M13mp9 (Messing et al., cited above). The recombinant phage, designated φRIT20300 was then used for mutagenesis experiments (Amersham system, supra) for the following S3 subunit mutations:

| Deletion | Oligonucleotide Sequence (5'-3') |
| --- | --- |
| Lys$^{10}$ | TGAACAGTGCCGGCGGGATG |
| Tyr$^{92}$ | GCCCGGTCTTTATGGTCGTG |
| Lys$^{93}$ | GTTGCCCGGTGTATATGGTC |
| Tyr$^{102}$ | CCTTGCTGTAGTGATCCGCA |
| Tyr$^{103}$ | TGACCTTGCTGTGATCCGCA |
| Lys$^{105}$ | TGGCCGTGACGCTGTAGTAG |

After mutagenesis, the site-specific mutants were sequenced to ensure that the correct mutation had been introduced. The double stranded replicative forms of the phage DNA were then isolated and digested with BglII and MluI. The 690 bp DNA fragments, containing the various S3 mutations, were then isolated.

A 2.7 kbp XmaI—EcoRI insert from plasmid pRIT13070 (cited above) was cloned into pUC9, a standard and commercially available cloning vector. This newly created plasmid, designated pPT3, was subsequently digested with BglII and MluI. Into this BglII—MluI site was ligated the 690bp BglII—MluI fragments from above, containing the various S3 mutations.

These recombinant plasmids, encoding for the various S3 mutations, were in turn digested with BamHI and BglII. The fragments, 1,750 bp in length, were isolated and ligated into the BamHI—BglII sites of pRIT13070. The various single S2 and S3 mutations are summarized in Table I below (mutations #1 to 9).

Example 3
Mutagenesis of S1

Digestion of pPTX42 (Locht et al., cited above) with the restriction enzyme Sau3A yielded, among others, a 560 bp fragment containing most of the coding region for the S1 pertussis toxin subunit, but lacking the carboxy terminus coding region. This fragment was isolated and ligated into the BamHI site of M13mp18 (Messing et al., cited above). The recombinant phage, designated φRIT20001 was then used for mutagenesis experiments via the Amersham "Oligonucleotide—Directed in vitro Mutagenesis Systems", supra.

To delete amino acid 26 (tryptophan), i.e., Trp$^{26}$ of subunit S1, the following synthetic oligonucleotide primer was used:

5'CGTTGTTTCCCGCCGTGAAT3'

After mutagenesis, the site-specific mutant was sequenced to ensure that the correct mutation had been introduced. The double stranded replicative form of the phage DNA was then isolated and digested with AccI. The 300 bp DNA fragment, containing the mutation in S1, was then isolated and ligated into the AccI site of pRIT13070 (cited above).

A similar procedure was used to introduce single amino acid deletions or substitutions of subunit S1 at positions 9(Arg), 13(arg), 35 (His), 40(Ser), and 129(Glu). The single mutations in the S1 subunit are listed in Table 1 below (mutations #11 to 22).

Example 4
Combination of mutations

The pRIT13070 derived plasmids from Example 1 (i.e., S2 mutants) are digested with XbaI and XmaI to yield 750 bp fragments which encode S2 mutations. The XbaI—XmaI fragments will replace the XbaI—XmaI fragment from pRIT13070 derived plasmids of Example 3 (i.e., S1 mutants) to yield a recombinant DNA molecule having mutations in subunits S1 and S2; e.g., Trp$^{26}$ (S1)—Asn$^{105}$ (S2). In a similar manner, the pRIT13070 derived plasmids of Example 2 (i.e., S3 mutants) can be digested with BglII and BamHT. The DNA fragments then isolated (approximately 1,750 bp) will replace the BglII—BamHT fragment from pRIT13070 derived plasmids of Example 3 (i.e., S1 mutants) to yield mutations in subunits S1 and S3; e.g., Trp$^{26}$ (S1)—Tyr$^{102-103}$ (S3). Furthermore, one skilled in the art is thus enabled to create additional combinations of S1, S1-S2, S1-S3, S2-S3, or S1-S2-S3 mutations based on this disclosure. The various combinations of mutations are listed in Table 1 below (mutations #10 and 23 to 31).

Example 5
Deletion of the toxin gene of a B. pertussis host

To express a pertussis toxin gene encoding one or more of the described mutations, it is desirable to first delete the wild-type B. pertussis toxin gene from the host cell. Thereby the toxin gene encoded by a plasmid will not recombine with the toxin gene encoded on the bacterial chromosome. Thus, the pertussis toxin coding sequence of the B. pertussis Tohama I vaccine strain was deleted in the following way:

The B. pertussis Tohama I strain (Sato, et al. in Manclark et al. (eds.), International Symposium on Pertussis, pp. 51–57, U.S. Department of Health, Education and Welfare, Washington, D.C. (1979), or Kasuga et al., Kitasato Arch. Exp. Med. 27: 57–62) was plated on BG medium (BG agar, Difco Laboratories (Detroit, Mich.), supplemented with defibrinated sheep blood 25% v/v) containing 400 μg/ml of streptomycin. The streptomycin resistant mutants were then plated on BG medium containing 50 μg/ml nalidixic acid. The colonies that arose, which were streptomycin and nalidixic acid resistant were then used for conjugation experiments.

Plasmid pTOX9 (Black et al., Infect Immun, 55: 2465–70 (1987)) contains the pertussis toxin gene on an approximately 10 kbp pertussis DNA fragment. Plasmid pTOX9 was digested with the restriction enzymes KpnI and BglII, then treated with Bal31 exonuclease, and finally religated. This resultant plasmid, in which the pertussis toxin gene was deleted, was subsequently digested with ClaI. This yielded an approximately 7 kbp fragment containing the flanking regions of a deleted pertussis toxin gene. This ClaI—ClaI fragment was end-filled, isolated and then ligated into the HindIII (end-filled) site of plasmid pSORTP1. Plasmid pSORTP1 was derived from plasmid pRTP1 (Stibitz et al., Gene, 50: 133–140 (1986)) in which the gentamicin gene has been inserted. Hence, pSORTP1 contains the gene for gentamicin resistance as well as the gene which confers sensitivity to streptomycin. Plasmid pSORTP1 does not autonomously replicate in B. pertussis, and therefore must recombine with the B. pertussis chromosome.

Prior to recombination, plasmid pSORTP1 containing the nucleotide sequences flanking the pertussis toxin gene, was introduced into E. coli strain SM10 (Simon et al., BioTechnology, 1: 784–791 (1983)). Several colonies were grown, and the plasmid DNA from each of those clones was individually analyzed by DNA sequence analysis to identify and verify the deletions.

An E. coli SM10 clone containing the recombinant plasmid pSORTP1 was conjugated with the wild-type B. pertussis Tohama I strain (disclosed above). This strain was streptomycin resistant (a recessive trait) and nalidixic acid resistant. The B. pertussis exconjugates were then plated onto BG agar plates containing nalidixic acid and gentamicin. The gentamicin resistant colonies, which were also streptomycin sensitive, could arise only if the entire recombinant plasmid was integrated into the B. pertussis chromosome. The gentamicin resistant clones were then plated onto BG plates containing 400 µg/ml streptomycin to select for a second recombination event resulting in streptomycin resistant B. pertussis revertants. These revertants arose due to a second homologous recombination between the chromosome and the inserted plasmid. Many of the resulting streptomycin resistant strains which were gentamicin sensitive again had lost the wild-type pertussis toxin via the recombination event. The colonies were analyzed by Southern blot hybridization to verify the loss of the wild-type pertussis toxin gene. The resulting B. pertussis strain, which lacks the pertussis toxin gene, was then used for-the expression of mutated pertussis toxin genes.

Example 6(a)
Expression of the Modified Pertussis Toxin Genes in B. pertussis with a replicating plasmid The pRIT13070 derived plasmids containing the described mutations in the S2 or S3 subunits were digested with the restriction enzyme EcoRI. The resulting 4.7 kbp fragments were ligated into the unique EcoRI site of plasmid PLAFRII (Friedman et al., Gene, 18: 289–296 (1982)). Plasmid pLAFRII contains a tetracycline resistance gene and therefore transformants with this plasmid can be selected on growth medium containing 12.5 µg/ml tetracycline. The recombinant plasmids were then introduced into E. coli SM10. The tetracycline resistant transformants were further analyzed by DNA sequencing for the presence of the mutated toxin genes. The colonies containing the desired mutations were conjugated with the B. pertussis strain, deleted in the pertussis toxin gene, as described in Example 5. Tetracycline resistant B. pertussis strains were then grown in modified Stainer-Scholte medium (Difco) containing 10 µg/ml tetracycline. The cells were then separated from the culture medium by centrifugation. The cells and the culture medium were both analyzed by Western blot using pertussis toxin specific monoclonal antibodies (see Francotte et al. in Vaccine 89, p. 243–247, Lerner et al., eds., Cold Spring Harbor Laboratory, Cold Spring Harbor, N.Y., 1989 and Frank et al., Infect Immun, 46: 195–201 (1984)).

For comparison, the wild-type B. pertussis strain (Tohama I) produced and secreted pertussis toxin into the culture media. The B. pertussis strain in which the pertussis toxin (PT) gene was deleted did not express a pertussis toxin. However, when this strain was transformed with a wild-type PT gene, carried by PLAFRII (supra), the PT was expressed at comparable, albeit somewhat lower levels as determined by ELISA as disclosed in Example 7. Clones containing the mutant pertussis toxin genes produced significant amounts, e.g., 1–4 µg/ml, of mutated toxin proteins which were shown to be secreted into the culture medium.

Example 6(b)
Expression of the modified pertussis toxin genes in B. pertussis with a plasmid integrated in the chromosome.

The pRIT 13070 derived plasmids containing the described mutations or combinations of these mutations were transformed by electroporation in B. pertussis deleted in the pertussis toxin gene (described in example 5). The electroporation was performed as follows. B. pertussis was grown in 10 ml of modified Stainer-Scholte medium till exponential phase. Cells were harvested by centrifugation, washed twice in ice-cold water and resuspended in 2 to 5 ml of water. 80 µl of this suspension and 2 µl of plasmid DNA were mixed and submitted to a single electrical pulse (2.5M , 200 Ω, 25 µF) in a 0.8 mm-gap cuvette electrode. The cells were directly transferred into 1 ml of medium, incubated at 37° C. for 1 to 4 hours and spread onto Bordet-Gengou plates containing ampicillin. As the pRIT 13070 derived plasmids are unable to replicate into B. pertussis, the ampicillin resistance can only be acquired by the integration of the plasmid by homologous recombination between the plasmid and the chromosome.

Ampicillin resistant B. pertussis strains were grown in modified Stainer-Scholte medium supplemented with 50 µg/ml of ampicillin. The cells were then separated from the medium by centrifugation. The supernatant was then analyzed by Western blot and ELISA using pertussis toxin-specific monoclonal and polyclonal antibodies (supra). Clones containing the mutant pertussis toxin genes produced significant amounts (0.5–10 µg/ml) of mutated toxin protein secreted into the culture medium.

Example 7
Biological Activity of the Modified Pertussis Toxin Polypeptides

The culture media of the various B. pertussis strains producing different genetically modified pertussis toxin proteins were analyzed by an enzyme-linked immunosorbent assay (ELISA) using haptoglobin-coated microtiter plates as described by Francotte et al. (supra). The absorbance was compared to the estimated concentration of the various toxin analogs in the culture medium. This analysis allowed identification of mutant proteins which possessed altered haptoglobin-binding activity. None of the mutations in the S3 subunit significantly altered the haptoglobin-binding ability of pertussis toxin. Mutations in the S2 subunit diminished the haptoglobin-binding capacity of pertussis toxin by various amounts. The mutant protein containing the deletion $Tyr^{102}$ in subunit S2 bound to haptoglobin with approximately 50% efficiency. The binding capacity of the PT protein containing a double deletion (i.e., $Tyr^{102-103}$) was reduced to approximately 4%, as compared to the wild type molecule; the haptoglobin-binding capacity of the PT protein containing the $Asn^{105}$ deletion was decreased to undetectable levels (i.e., less than 0.5% of the wild type activity).

These results indicate that Asn$^{105}$ of the S2 subunit is essential for haptoglobin-binding. The analogous mutation in the S3 subunit (Lys$^{105}$) did not affect the haptoglobin-binding capacity, suggesting that the binding of the toxin to haptoglobin and haptoglobin-like receptors occurs specifically via Dimer 1 (i.e., subunits S2 and S4).

As indicated above, Dimer 2 (subunits S3 and S4) appears to specifically bind to CHO cell membranes (Brennan et al., supra). Therefore, pertussis toxin analogs containing alterations in the S3 subunit may affect this CHO-cell specific cytotoxicity. The mutant proteins analyzed in these examples exhibited reduction in cytotoxicity, and the deletions Tyr$^{102-103}$ and Lys$^{105}$ in subunit S3 exhibited significant reduction in such cytotoxicity. For these deletions, i.e., Tyr$^{102-103}$ and Lys$^{105}$ Lys$^{105}$, no cytotoxicity was detectable in the culture medium, indicating an apparent detoxification factor of at least 100 fold. It is further noted that all of the mutant proteins were recognized by monoclonal antibodies to the individual subunits.

Example 8
Parenteral Vaccine preparation

5–25 μg of mutated toxin protein, prepared according to the method of Example 6, is mixed with an aluminum adjuvant, such as aluminum hydroxide, to produce a vaccine in a form appropriate for incorporation into a parenteral administration dosage form.

It is appreciated that the invention is not limited to the particular embodiments described above in the Examples. All embodiments of the invention, therefore, are believed to come within the scope of the following claims.

TABLE 1

| Mutation # | S1 | S2 | S3 | pRIT13070 derived plasmids |
|---|---|---|---|---|
| 1 | | Tyr102->Δ102 | | pPTΔs2Y102 |
| 2 | | Tyr102-103 ->Δ102-103 | | pPTΔs2Y102-103 |
| 3 | | Asn105->Δ105 | | pPTΔs2N105 |
| 4 | | | Lys10->Δ10 | pPTΔs3K10 |
| 5 | | | Tyr2->Δ92 | pPTΔs3Y92 |
| 6 | | | Lys93->Δ93 | pPTΔs3K93 |
| 7 | | | Tyr102->Δ102 | pPTΔs3Y102 |
| 8 | | | Tyr102-103 ->Δ102-103 | pPTΔs3Y102-103 |
| 9 | | | Lys105->Δ105 | pPTΔs3K105 |
| 10 | | Asn105->Δ105 | Lys105->Δ105 | pPT-NK |
| 11 | Arg9->Δ9 | | | pPTS1R9Δ |
| 12 | Arg9->Lys9 | | | pPTS1R9K |
| 13 | Arg13->Δ13 | | | pPTS1R13Δ |
| 14 | Arg13->Leu13 | | | pPTS1R13L |
| 15 | W26->Δ26 | | | pPTS1W26Δ |
| 16 | W26->Thr26 | | | pPTS1W26T |
| 17 | W26->Ile26 | | | pPTS1W26I |
| 18 | His35->Δ35 | | | pPTS1H35Δ |
| 19 | Ser40->Δ40 | | | pPTS1S40Δ |
| 20 | Glu129->Δ129 | | | pPTS1E29Δ |
| 21 | Glu129->Asp129 | | | pPTS1E129D |
| 22 | Glu129->Gly129 | | | pPTS1E129G |
| 23 | W26->Δ26 Glu129->Asp129 | | | pPTS1W26Δ/E129D |
| 24 | W26->Thr26 Glu129->Δ129 | | | pPTS1W26T/E129Δ |
| 25 | W26->Thr26 Glu129->Asp129 | | | pPTS1W26T/E129D |
| 26 | Arg9->Lys9 Glu129->Gly 129 | | | pPTS1R9K/E129G |
| 27 | Arg13->Leu13 Glu129->Gly 129 | | | pPTS1R13L/E129G |
| 28 | W26->Ile26 Glu129->Gly 129 | | | pPTS1W26I/E129G |
| 29 | Arg9->Lys9 Glu129->Gly 129 | Asn105->Δ105 | Lys105->Δ105 | pPT-R9ENK |
| 30 | Arg13->Leu13 Glu129->Gly 129 | Asn105->Δ105 | Lys105->Δ105 | pPT-R13ENK |
| 31 | W26->Ile26 Glu129->Gly 129 | Asn105->Δ105 | Lys105->Δ105 | pPT-WENK |

What is claimed is:

1. An isolated DNA molecule comprising a recombinant coding sequence encoding all of a *Bordetella pertussis* holotoxin or portion thereof wherein said holotoxin or portion thereof comprises either or both of a modified S2 subunit protein and a modified S3 subunit protein, wherein said modified subunit protein is specifically reactive against a wild-type pertussis toxin but is defective in pertussis toxin target cell receptor binding, and wherein:

said modified S2 subunit comprises one or more amino acid sequence mutations selected from the group consisting of a deletion of one or more of Tyr$^{102}$, Tyr$^{103}$ and Asn$^{105}$, an amino acid substitution of either or both of Tyr$^{102}$ and Tyr$^{103}$, and a substitution of a negatively-charged amino acid for Asn$^{105}$, and said modified S3 subunit comprises one more amino acid sequence mutations selected from the group consisting of a deletion of one or more of Tyr$^{102}$, Tyr$^{103}$ and

19

Lys$^{105}$, an amino acid substitution of either or both of Tyr$^{102}$ and Tyr$^{103}$, and a substitution of a negatively-charged amino acid for Lys$^{105}$.

2. The DNA molecule of claim 1 which encodes a modified B. pertussis toxin B-oligomer.

3. The DNA molecule of claim 2 which encodes a modified B. pertussis toxin comprising a modified dimer D1 coding sequence and lacking S1, S3, and S5 subunit coding sequences.

4. The DNA molecule of claim 2 which encodes a modified B. pertussis toxin comprising a modified dimer D2 coding sequence and lacking S1, S2, and S5 subunit coding sequences.

5. The DNA molecule of claim 2 which encodes a modified B. pertussis toxin comprising a modified dimer D1 coding sequence, a wild-type dimer D2 coding sequence, and a wild-type subunit S5 coding sequence.

6. The DNA molecule of claim 5 wherein the S2 subunit of said modified dimer D1 is modified by a deletion of Tyr$^{102}$.

7. The DNA molecule of claim 5 wherein the S2 subunit of said modified dimer D1 is modified by deletions of Tyr$^{102}$ and Tyr$^{103}$.

8. The DNA molecule of claim 5 wherein the S2 subunit of said modified dimer D1 is modified by a deletion of Asn$^{105}$.

9. The DNA molecule of claim 5 wherein the S2 subunit of said modified dimer D1 is modified by a substitution of Asn$^{105}$ with a negatively-charged amino acid.

10. The DNA molecule of claim 9 wherein the S2 subunit of said modified dimer D1 is modified by a substitution of Asn$^{105}$ with Asp.

11. The DNA molecule of claim 2 which encodes a modified B. pertussis toxin comprising a modified dimer D2 coding sequence, a wild-type dimer D1 coding sequence, and a wild-type subunit S5 coding sequence.

12. The DNA molecule of claim 11 wherein the S3 subunit of said modified dimer D2 is modified by a deletion of Tyr$^{102}$.

13. The DNA molecule of claim 11 wherein the S3 subunit of said modified dimer D2 is modified by deletions of Tyr$^{102}$ and Tyr$^{103}$.

14. The DNA molecule of claim 11 wherein the S3 subunit of said modified dimer D2 is modified by a deletion of Lys$^{105}$.

15. The DNA molecule of claim 2 which encodes a modified B. pertussis toxin comprising a modified dimer D2 coding sequence, a modified dimer D1 coding sequence, and a wild-type subunit S5 coding sequence.

16. The DNA molecule of claim 15 wherein said modified dimer D1 coding sequence comprises a deletion of Asn$^{105}$ and said modified dimer D2 coding sequence comprises a deletion of Lys$^{105}$.

17. A recombinant plasmid which comprises the DNA molecule of claim 1 operatively linked to a regulatory region.

18. A host cell transformed with the recombinant plasmid of claim 17, wherein said host cell is selected from the group consisting of a yeast cell, an insect cell, a mammalian cell, an E. coli cell, a Streptomyces cell, a Bacillus cell, and a Salmonella cell.

19. The host cell of claim 18 which is E. coli.

20. A transformed host cell comprising the recombinant DNA molecule of claim 1 integrated into the genome of the host cell, wherein said host cell is selected from the group consisting of a yeast cell, an insect cell, a mammalian cell, an E. coli cell, a Streptomyces cell, a Bacillus cell, and a Salmonella cell.

21. A transformed host cell comprising the recombinant DNA molecule of claim 1 integrated into the genome of the host cell wherein said host cell is a Bordetella pertussis cell and wherein the genomic integration of said recombinant DNA molecule results in the expression of an inactive pertussis toxin.

22. A process for preparing a Bordetella pertussis holotoxin or portion thereof encoded by the DNA molecule of claim 1 which comprises:

(a) transforming a host cell selected from the group consisting of a yeast cell, an insect cell, a mammalian cell, an E. coli cell, a Streptomyces cell, a Bacillus cell, and a Salmonella cell with the recombinant DNA molecule of claim 1, and, (b) growing said transformed host cell in a suitable culture medium.

23. The process of claim 22 which further comprises isolating the Bordetella pertussis holotoxin or portion thereof so produced.

24. A Bordetella pertussis holotoxin or portion thereof produced by the process of claim 23.

25. A Bordetella pertussis holotoxin or portion thereof encoded by the DNA molecule of claim 1.

26. A whole cell vaccine for stimulating protection against whooping cough wherein such vaccine comprises an immunoprotective and non-toxic quantity of the host cells of claim 18 or 19.

27. A whole cell vaccine for stimulating protection against whooping cough wherein such vaccine comprises an immunoprotective and non-toxic quantity of inactivated host cells of claim 21.

28. A vaccine for stimulating protection against whooping cough wherein such vaccine comprises an immunoprotective and non-toxic quantity of the Bordetella pertussis holotoxin or portion thereof of claim 25.

29. A vaccine for stimulating protection against whooping cough wherein such vaccine comprises an immunoprotective and non-toxic quantity of the Bortella pertussis holotoxin or portion thereof produced by the process of claim 23.

30. A method for protecting a human against disease symptoms associated with whooping cough infection which comprises administering to such human a safe and effective amount of the vaccine of claim 28.

31. A method for protecting a human against disease symptoms associated with whooping cough infection which comprises administering to such human a safe and effective amount of the vaccine of claim 29.

* * * * *